United States Patent
Aben et al.

(10) Patent No.: US 9,811,939 B2
(45) Date of Patent: Nov. 7, 2017

(54) METHOD AND SYSTEM FOR REGISTERING INTRAVASCULAR IMAGES

(71) Applicant: Pie Medical Imaging B.V., Maastricht (NL)

(72) Inventors: Jean-Paul Aben, Limbricht (NL); Boudewijn J. A. Verstraelen, Lanaken (BE); Tristan Slots, Maasmechelen (BE)

(73) Assignee: Pie Medical Imaging B.V., Maastricht (NL)

( * ) Notice: Subject to any disclaimer, the term of this patent is extended or adjusted under 35 U.S.C. 154(b) by 40 days.

(21) Appl. No.: 14/537,425

(22) Filed: Nov. 10, 2014

(65) Prior Publication Data
US 2015/0131886 A1    May 14, 2015

(30) Foreign Application Priority Data
Nov. 13, 2013  (EP) ...................................... 13192749

(51) Int. Cl.
*G06K 9/00*    (2006.01)
*G06T 15/00*    (2011.01)
(Continued)

(52) U.S. Cl.
CPC ................ *G06T 15/00* (2013.01); *A61B 6/12* (2013.01); *A61B 6/487* (2013.01); *A61B 6/504* (2013.01);
(Continued)

(58) Field of Classification Search
CPC . G06T 2207/10121; G06T 2207/30101; G06T 2207/20101; G06T 2207/30172;
(Continued)

(56) References Cited

U.S. PATENT DOCUMENTS 7,729,746 B2    6/2010    Redel et al.
8,298,147 B2 *  10/2012   Huennekens .......... A61B 6/504
                                                   382/128
(Continued)

OTHER PUBLICATIONS

Wahle, Andreas, et al. "Geometrically correct 3-D reconstruction of intravascular ultrasound images by fusion with biplane angiography-methods and validation." Medical Imaging, IEEE Transactions on 18.8 (1999): 686-699.*

(Continued)

*Primary Examiner* — Jonathan S Lee
(74) *Attorney, Agent, or Firm* — Gordon & Jacobson, P.C.

(57) ABSTRACT

A method for co-registration of angiography and intravascular images is described in which intravascular images are in the form of a sequence of images obtained from an intravascular imaging device which is pulled back through a vessel. The method includes generating a three-dimensional reconstruction of the trajectory of the intravascular device within the vessel from two or more bi-dimensional angiography images of such vessel which have been obtained from different perspectives. The method also includes determining a first position of an element of the device within the 3D reconstruction of the trajectory and correlating the position of such element with a correspondent point in the reconstructed trajectory during pull back. Further, the method includes correlating each intravascular image of the sequence with a corresponding spatial position within at least one of the bi-dimensional angiography images. A corresponding system and computer program are also described.

28 Claims, 10 Drawing Sheets

(51) Int. Cl.
*A61B 6/12* (2006.01)
*A61B 8/12* (2006.01)
*G06T 7/32* (2017.01)
*A61B 6/00* (2006.01)
*A61B 8/08* (2006.01)

(52) U.S. Cl.
CPC .......... *A61B 6/5247* (2013.01); *A61B 8/0891* (2013.01); *A61B 8/12* (2013.01); *A61B 8/5261* (2013.01); *G06T 7/32* (2017.01); *A61B 6/4441* (2013.01); *A61B 6/481* (2013.01); *A61B 6/541* (2013.01); *A61B 8/0883* (2013.01); *G06T 2207/10101* (2013.01); *G06T 2207/10116* (2013.01); *G06T 2207/10132* (2013.01); *G06T 2207/30101* (2013.01); *G06T 2207/30241* (2013.01)

(58) Field of Classification Search
CPC . G06T 2207/30204; G06T 2207/30021; G06T 7/0024; G06T 2207/10116; G06T 2207/30241
See application file for complete search history.

(56) References Cited

U.S. PATENT DOCUMENTS

| | | | |
|---|---|---|---|
| 8,411,927 B2 | 4/2013 | Chang et al. | |
| 8,600,138 B2* | 12/2013 | Gorges | G06T 11/006 382/131 |
| 8,892,186 B2* | 11/2014 | Wu | G06T 7/0014 600/424 |
| 9,002,436 B2* | 4/2015 | Wu | A61B 6/12 382/128 |
| 9,195,905 B2* | 11/2015 | Wang | G06K 9/469 |
| 9,220,467 B2* | 12/2015 | Wu | G06T 7/251 |
| 2008/0137926 A1* | 6/2008 | Skinner | G06K 9/34 382/131 |
| 2009/0279767 A1* | 11/2009 | Kukuk | G06T 7/74 382/132 |
| 2011/0034801 A1 | 2/2011 | Baumgart | |
| 2011/0230758 A1* | 9/2011 | Eichler | A61B 5/06 600/424 |
| 2012/0059253 A1* | 3/2012 | Wang | A61B 6/00 600/427 |
| 2014/0094691 A1* | 4/2014 | Steinberg | A61B 5/7425 600/424 |
| 2014/0094692 A1* | 4/2014 | Tolkowsky | A61B 5/064 600/424 |
| 2014/0099012 A1* | 4/2014 | Begin | G06T 5/006 382/131 |
| 2014/0193057 A1* | 7/2014 | Zagrodsky | G06T 7/0012 382/131 |
| 2014/0270436 A1* | 9/2014 | Dascal | A61B 5/0035 382/130 |
| 2014/0275996 A1* | 9/2014 | Stigall | A61B 6/5247 600/424 |
| 2016/0196666 A1* | 7/2016 | Venkatraghavan | G06T 7/254 382/130 |

OTHER PUBLICATIONS

Godbout, Benoit, et al. "3D elastic registration of vessel structures from IVUS data on biplane angiography." Academic radiology 12.1 (2005): 10-16.*
Slager, Cornelis J., et al. "True 3-dimensional reconstruction of coronary arteries in patients by fusion of angiography and IVUS (ANGUS) and its quantitative validation." Circulation 102.5 (2000): 511-516.*
Wang, Peng, et al. "Image-based co-registration of angiography and intravascular ultrasound images." IEEE transactions on medical imaging 32.12 (2013): 2238-2249.*
"A novel method for detecting R-peaks in electrocardiogram (ECG) signal", M. Sabarimalai, K.P. Soman, Biomedical Signal Processing and Control (2011).
Introduction to Catmull-Rom splines, Robert Dunlop, available at http://www.mvps.org/directx/articles/catmull, 2005.
"A novel dedicated 3-dimensional quantitative coronary analysis methodology for bifurcation lesions", Yoshinobu Onuma et al., EuroIntervention 2011; 6:1-00.
Fusion of 3D QCA and IVUS/OCT, The International Journal of Cardiovascular Imaging, vol. 27, No. 2, Feb. 2, 2011.

* cited by examiner

METHOD AND SYSTEM FOR REGISTERING INTRAVASCULAR IMAGES

CROSS-REFERENCE TO RELATED APPLICATIONS

The present application claims priority from EP 13192749.3, filed on Nov. 13, 2013, herein incorporated by reference in its entirety.

BACKGROUND

1. Field

The invention relates to medical imaging, particularly in percutaneous interventions.

2. State of the Art

During percutaneous treatment of vascular diseases, X-ray angiographic imaging is used to guide the intervention procedure. Detailed information of the diseased vessel, for example atherosclerotic plaque, is assessed by intravascular imaging modalities, such as intravascular ultrasound (IVUS) or optical coherence tomography (OCT), during the intervention procedure. Another example of an intravascular imaging modality is intravascular fractional flow reserve (FFR) in which the pressure within the vessel is measured during pullback.

The subject invention relates to all intravascular imaging devices having a controlled pullback speed. Intravascular imaging is performed during pullback of an intravascular device through a vessel and produces a stack of images showing vessel cross sections.

With this imaging modality it is difficult to correlate the position of a particular image with respect to its location in the vessel within an angiographic view. In practice the physician looks for anatomical landmarks, for example bifurcations or a number of side branches that can be recognized both on X-ray angiography and on the intravascular images in order to correlate the information of both imaging modalities with each other. However, this is time-consuming and prone to errors which might not lead to optimal treatment of vessel diseases.

US Patent Application Publication No. 2012/0059253 relates to a method of co-registration of intravascular images with X-ray images by tracing the intravascular transducer, which is located on the tip of the guide-wire, during pullback on X-ray fluoroscopy. This method has the disadvantage that the patient has an additional X-ray exposure, since X-ray fluoroscopy is necessary during the complete pullback of the intravascular device. During a percutaneous coronary intervention procedure, for example, the length of the coronary artery of interest can be up to 15 cm. With a motorized pullback speed of 0.5 mm/sec this would lead to an additional X-ray exposure time of 5 min. Although X-ray exposure can be reduced by means of ECG gated X-ray imaging, still the patient receives additional X-ray exposure. Another disadvantage of this method is the limited accuracy of length assessment due to foreshortening or out-of-plane magnification errors, which is important when choosing the correct stent- and/or balloon-length during treatment of the vascular disease.

U.S. Pat. No. 7,729,746 relates to a method in which the co-registration between X-ray and intravascular images is performed by generation of a 3D reconstruction of the vessel based on two X-ray angiographic projections. In order to perform the co-registration, two additional X-ray fluoroscopic images are required in which the user identifies in each fluoroscopic image the tip of the intravascular transducer. This results in a 3D point in space which is used to perform the co-registration. This approach goes in the right direction since the 3D reconstruction of the vessel of interest eliminates foreshortening and out-of-plane magnification errors, although the incorrect assumption is made that the centerline of the 3D model corresponds with the intravascular path in the vessel during pullback. Furthermore, any errors in the 2D segmentation of the vessel within the X-ray angiographic images will negatively influence the co-registration since they directly affect the 3D reconstruction of the vessel and its resulting centerline. Another disadvantage is that four additional X-ray images are required for this method resulting in additional exposure to the patient.

A further disadvantage of the prior art is that the true imaging plane within the space occupied by the intravascular electronics is not taken into consideration.

SUMMARY

The subject invention improves the registration process of intravascular and angiographic images by, at least partially, overcoming the above-noted drawbacks.

According to one aspect, a method is provided for registering intravascular images that fits well in an interventional procedure with a reduced burden for the patient both in terms of X-ray and contrast agent exposure.

In one embodiment a method is described for co-registration of angiography and intravascular images, which intravascular images are in the form of a sequence of images obtained from an intravascular imaging device which is pulled back through a vessel. The method comprises the steps of:
  a) generating a three-dimensional reconstruction of a trajectory of the intravascular device within the vessel, either automatically or manually by fitting user indicated points, from two or more bi-dimensional angiography images of such vessel which have been obtained from different perspectives;
  b) determining a first position of an element of the device within the 3D reconstruction of the trajectory;
  c) correlating the position of such element with a correspondent point in the reconstructed trajectory during pull back; and
  d) correlating each intravascular image of the sequence with a corresponding spatial position within at least one of the bi-dimensional angiography images.

The co-registration can be performed after the intravascular pullback or just before the intravascular pullback. The latter allows real time feedback of position of intravascular image in the X-ray images during the intravascular pullback.

The angiography images are typically bi-dimensional X-ray images obtained with or without contrast agents. Specifically, as there is no need to reconstruct the vessel wall as well as the centerlines as in the prior art, such images can be obtained without contrast agents, i.e. they can be so-called fluoroscopic images. The trajectory of the intravascular device can be, in fact, advantageously reconstructed by following the position of the wire of the catheter associated with the intravascular device starting from the tip once in the start of examination position, hence no contrast enhancement is necessary.

Typically, as one of the advantages of the method of the invention resides in the fact that it can fit well in the intervention procedure, one of the at least two angiography images is preferably the same angiographic image (i.e. obtained with a contrast agent) that is usually acquired during common catheterization laboratory workflow of a percutaneous intervention procedure. This allows a reduction in X-ray exposure to the patient. The second image, obtained from a different perspective, does not require contrast agent and thus can advantageously be a fluoroscopic image.

According to one aspect of the subject invention co-registration is performed by using the 3D reconstruction of the trajectory of the intravascular device, and not the 3D reconstruction of the vessel, obtained from two angiography images in which the start of the 3D trajectory of the intravascular device is the intravascular device itself and this will correspond with the first intravascular image.

Furthermore, an accurate match with the true position of the intravascular imaging plane with respect to its location as visible on fluoroscopy and/or angiography can be obtained by using the technical specifications of the intravascular imaging device used during the procedure. To such extent, the element of the device, whose first position is determined within the 3D reconstruction of the trajectory to correlate the position of the device in the reconstructed trajectory during pull back, can advantageously be a marker or any position on proximal side or distal side of the device having a known distance to the imaging plane of the intravascular device.

This means that co-registration can be automatically performed between angiography imaging and intravascular imaging in a very easy and effective way for immediate use during normal catheterization procedures. Furthermore, the co-registration is based on the true 3D trajectory of the intravascular device resulting in a perfect length assessment allowing accurate length measurement to support the clinician in appropriate interventional treatment.

According to an embodiment, a so-called longitudinal image is shown wherein the intravascular images acquired during pull back are stacked on each other along a longitudinal line, the position of each intravascular image within the vessel being identified by a marker on the line and a corresponding marker in the angiography image.

In another embodiment, the degree of perpendicularity of the acquired intravascular images with reference to the vessel can be determined by calculating planes perpendicular to the reconstructed trajectory and back projecting such planes on the angiography image. Such degree of perpendicularity can be evaluated, for example, by comparing the orientation of the planes perpendicular to the reconstructed trajectory with corresponding planes perpendicular to the lumen boundary of the vessel on the angiography image. The orientation of the planes perpendicular to the trajectory and to the lumen boundary can be shown as markers in the form of segments on the angiography image. The degree of perpendicularity can also be advantageously quantified using a colour-coded representation on the angiography image. This allows for immediate correction of overestimated areas within the vessel.

The invention also relates to a computer product directly loadable into the memory of a computer and comprising software code portions for performing the method as disclosed above when the product is run on a computer.

According to another aspect, the invention relates to a system for registering angiography and intravascular images of a vessel having processing means configured to perform the method as disclosed above to register intravascular images with at least one angiographic image.

Particularly the system includes an imaging apparatus for acquiring intravascular images of the vessel, means for storing and/or receiving at least two angiography images of the vessel, and a combination device for registering the intravascular images with at least one of the angiography images. The imaging apparatus includes an intravascular device to be deployed in the vessel to a start of examination location for acquiring images of the vessel when pulling back such device from such location. The pulling back is performed at a controlled speed through a motorized pulling element. The combination device is adapted to perform the method according to the invention, for example by:

a) generating a three-dimensional reconstruction of a trajectory of the intravascular device within the vessel from two or more bi-dimensional angiography images of such vessel which have been obtained from different perspectives. The reconstructed trajectory typically has a starting point related to the start of examination position of the imaging device;

b) determining a first position of an element of the device within the 3D reconstruction of the trajectory, the element being, for example, a marker or any position on proximal side or distal side of the device having a known distance to the imaging plane;

c) correlating the position of such element with a correspondent point in the reconstructed trajectory during pull back; and d) correlating each intravascular image of the sequence with a corresponding spatial position within at least one of the bi-dimensional angiography images.

According to an embodiment, the system can be provided in combination with an X-ray apparatus for acquiring two or more bi-dimensional angiography images of a vessel of a patient from different perspectives. The X-ray apparatus can be a dual arm X-ray apparatus to acquire biplane angiography images or a single arm X-ray apparatus to acquire single plane fluoroscopic and/or angiographic images.

DETAILED DESCRIPTION

The invention is particularly advantageous in image guidance during minimally invasive cardiovascular interventions based on 2D angiographic film of X-ray images and it will be mainly disclosed with reference to this field. Examples of such interventions are percutaneous coronary interventions (PCI). Intravascular images can be obtained with any kind of intravascular imaging modality during the intervention procedure such as intravascular ultrasound (IVUS), optical coherence tomography (OCT) or fractional flow reserve (FFR) which can have a controlled pullback speed. FFR will result in a number of values representing the local pressure at each position during the pullback.

The co-registration can be performed after the intravascular pullback or just before the intravascular pullback. The latter allows real time feedback of position of intravascular image in the X-ray images during the intravascular pullback.

For accurate co-registration between intravascular and angiography, the true pullback length during intravascular imaging is required from the angiography images. Since angiography produces 2D images, length measurements are prone to errors due to foreshortening and out-of-plane magnification effects. The true pullback length of intravascular device is assessed by a 3D reconstruction of the catheter wire of the intravascular device which is visible in two angiography images. By using the 3D reconstruction of the intravascular catheter-path instead of the 3D centerline from the 3D reconstruction of the vascular lumen, co-registration errors are avoided in tortuous vessel which is common anatomy in coronary vessels.

Figure 1:
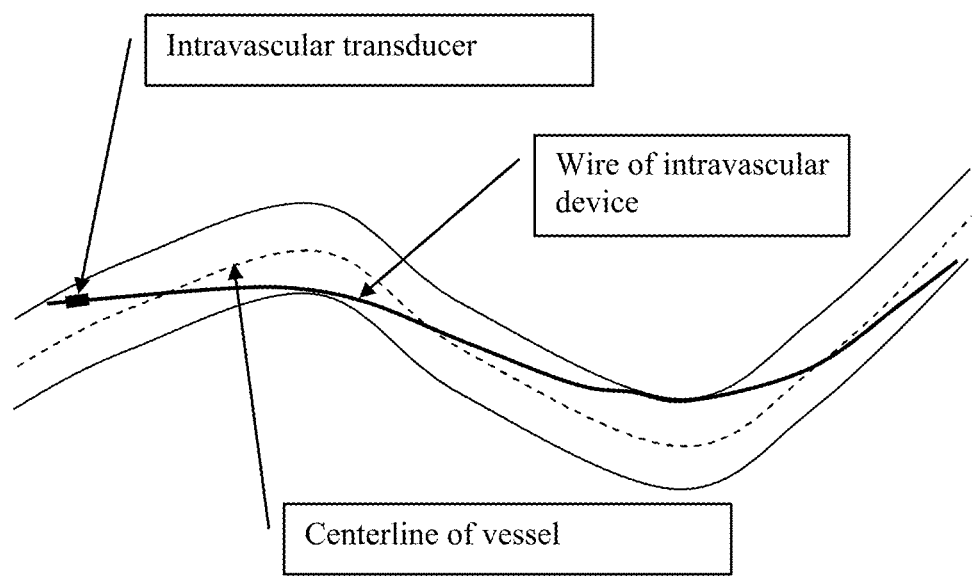
FIG. 1 shows a schematic representation of an X-ray image in which an intravascular device has been percutaneously inserted in the vessel.

FIG. 1 is a schematic representation of an angiography image of a vessel with an inserted intravascular device: due to tortuousity, the centerline of the vessel follows a different route with reference to the position of the catheter wire.

Figure 2:
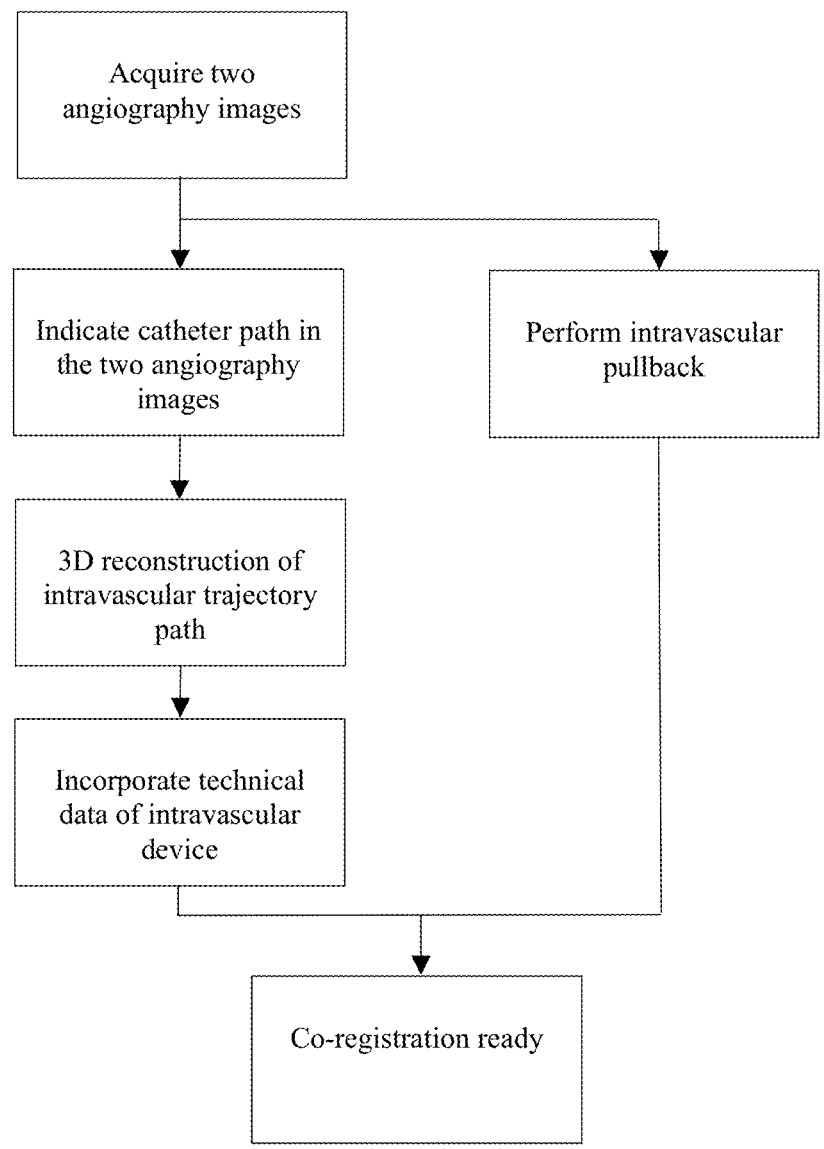
FIG. 2 is a flowchart of the invention main steps in a first embodiment where co-registration is performed after pullback.
Figure 3:
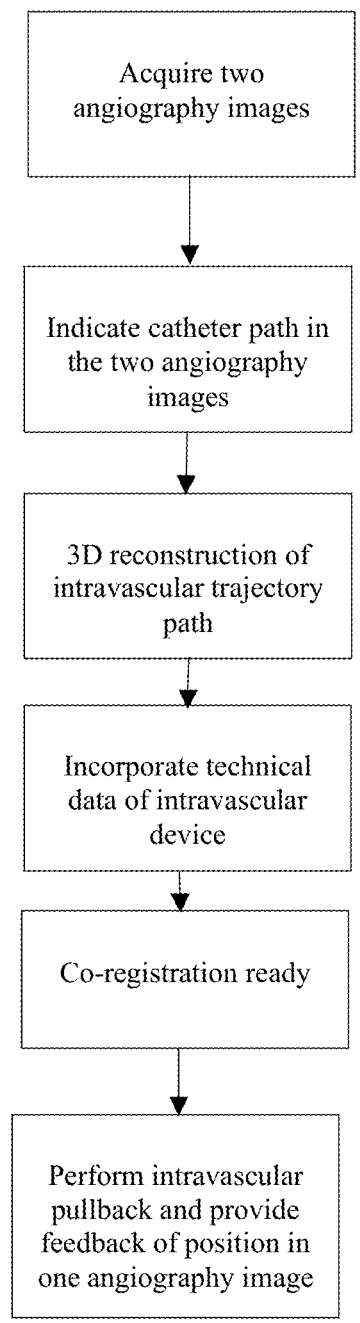
FIG. 3 is a flowchart of the invention main steps in a second embodiment where co-registration is performed before pullback, allowing visual feedback of position of intravascular imaging device on x-ray during the pullback.

With reference to the flowchart diagrams of FIGS. 2 and 3, which respectively show the workflow when co-registration is performed after or before pullback, the steps of two embodiments of the invention are now described.

Step 1: Acquire Two Angiography Images

The angiography images are typically bi-dimensional X-ray images obtained, with or without contrast agents, when the intravascular device is in its start of examination position, i.e. it has been placed in the vessel of interest to perform intravascular imaging during pull back of the same. Any image device capable of providing 2D images can be used for the purpose. For example a bi-plane or single plane angiographic system can be used such as those manufactured, for example, by Siemens (Artis zee Biplane) or Philips (Allura Xper FD). In case of a single arm X-ray system, one X-ray angiographic image is used which shows the vessel of interest and the intravascular device which is common during catheterization laboratory workflow of percutaneous coronary intervention. The second X-ray image is a fluoroscopic image of the intravascular device inserted in the vessel to avoid the use of additional contrast agent. In case of a dual arm X-ray system, an additional fluoroscopic X-ray image is not necessary and the biplane images are directly used to perform the 3D reconstruction of the catheter path.

Step 2: Indicate Catheter Path in the Two Angiography Images

Figure 4:
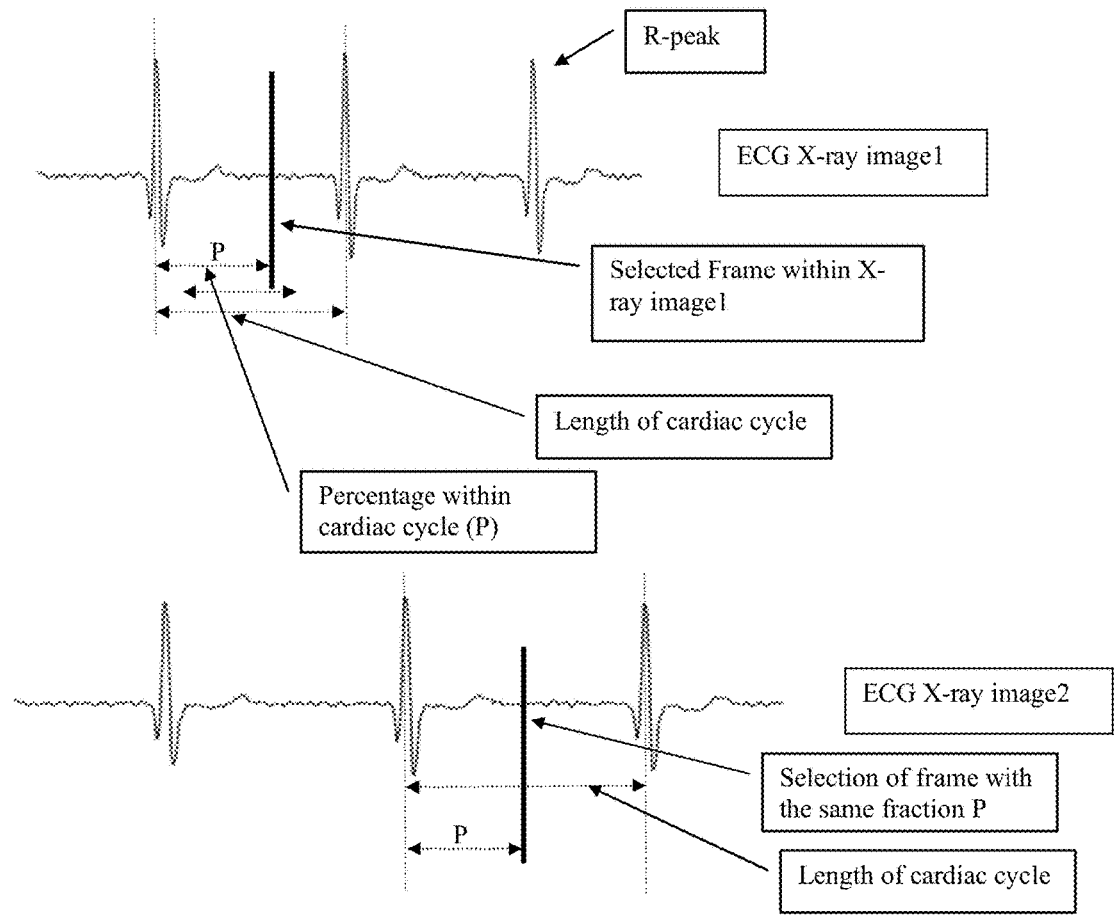
FIG. 4 shows how ECG signal can be used to match information on angiography images.

In both X-ray images (for example fluoroscopic and angiographic or biplane angiographic), the catheter path is indicated starting at the intravascular transducer. In case of a single X-ray system, the corresponding frame of the second X-ray image can be automatically selected by matching the corresponding frame based on the ECG signal within the first X-ray image. This is achieved by detection of the length of the cardiac cycle, for example as disclosed in "A novel method for detecting R-peaks in electrocardiogram (ECG) signal", M. Sabarimalai, K. P. Soman, Biomedical Signal Processing and Control (2011), doi:10.1016/j.bspc.2011.03.004. Next, a percentage is calculated within the cardiac cycle corresponding to the frame of the first X-ray image. In the second X-ray image a frame is selected with the same percentage within the cardiac cycle based on ECG signal belonging to the second X-ray image as shown in FIG. 4.

The indication of the intravascular catheter in the X-ray images can be performed quickly, for example, by using the parametric Catmull-Rom 2D spline fitting through several user indicated points. The Catmull-Rom 2D spline is disclosed, for example, in "A Class of Local Interpolating Splines", E. Catmull and A. Rom, Computer Aided Geometrical Design, 1974, pages 317-326. See also the article by Robert Dunlop that can be found on the Internet at http://www.mvps.org/directx/articles/catmull. An automatic path recognition algorithm can be equally employed.

Figure 5:
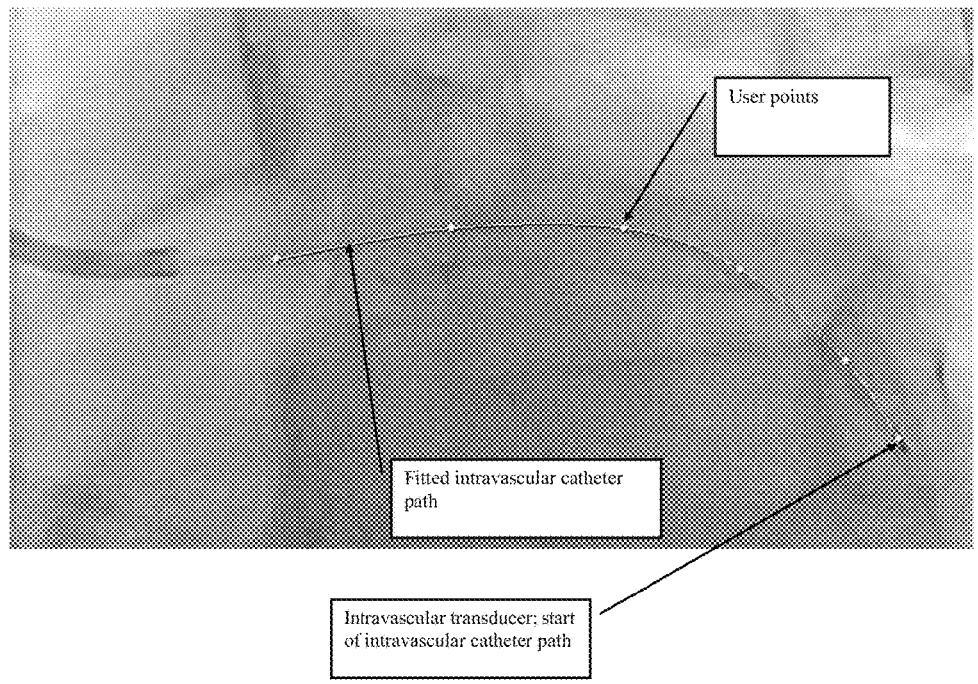
FIG. 5 shows the intravascular catheter wire on a fluoroscopic 2D X-ray image once the intravascular transducer has been inserted.
Figure 6:
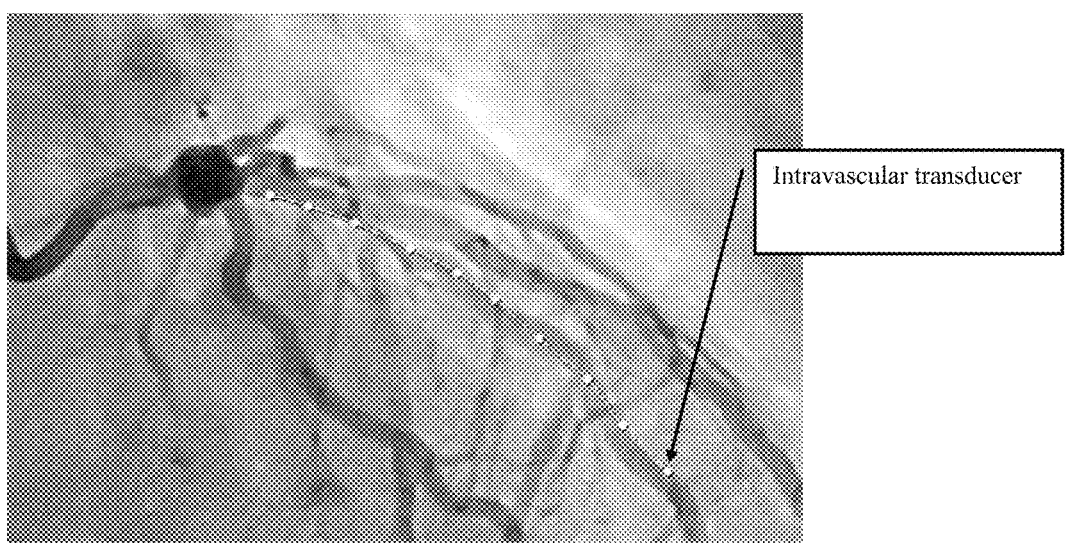
FIG. 6 shows the same intravascular catheter wire as in FIG. 5 on an angiographic 2D X-ray image.

The result is shown in FIGS. 5 and 6: the catheter wire of the intravascular device is outlined on both 2D angiography images.

Step 3: 3D Reconstruction of Trajectory of the Intravascular Transducer

The 3D trajectory (hereinafter referred also as path) of the intravascular device is reconstructed by a 3D reconstruction of the intravascular catheter wire, and starting at the tip of the intravascular device.

The 3D reconstruction of the path can be performed by using epipolar 3D reconstruction techniques, for example as disclosed in "A novel dedicated 3-dimensional quantitative coronary analysis methodology for bifurcation lesions", Yoshinobu Onuma, Chrysafios Girasis, Jean-Paul Aben, Giovanna Sarno, Nicolo Piazza, Coen Lokkerbol, Marie-Angel Morel, Patrick W. Serruys, EuroIntervention 2011; 6:1-00.

In case the first position within the 3D reconstruction of the catheter wire does not reflect the position of the intravascular device, an addition point within one of the X-ray images is required to define the location of the intravascular device within the 3D reconstruction of the intravascular catheter wire.

Step 4: Incorporate Technical Data of Intravascular Device

This step is completely optional and aims at increasing accuracy.

Intravascular imaging is typically performed with a catheter having on the tip an imaging device, such as a transducer in case of IVUS, which absorbers X-ray radiation and therefore is visible both on fluoroscopy and angiography. Although the device is normally manufactured as small as possible, it still occupies physical space. For example, for an IVUS device this can be up to 10 mm. Within this space, the true imaging plane is somewhere located. By using the technical specification provided by the intravascular device manufacturer, the position of such plane can be determined and thus used to increase the accuracy of the co-registration.

Figure 7:
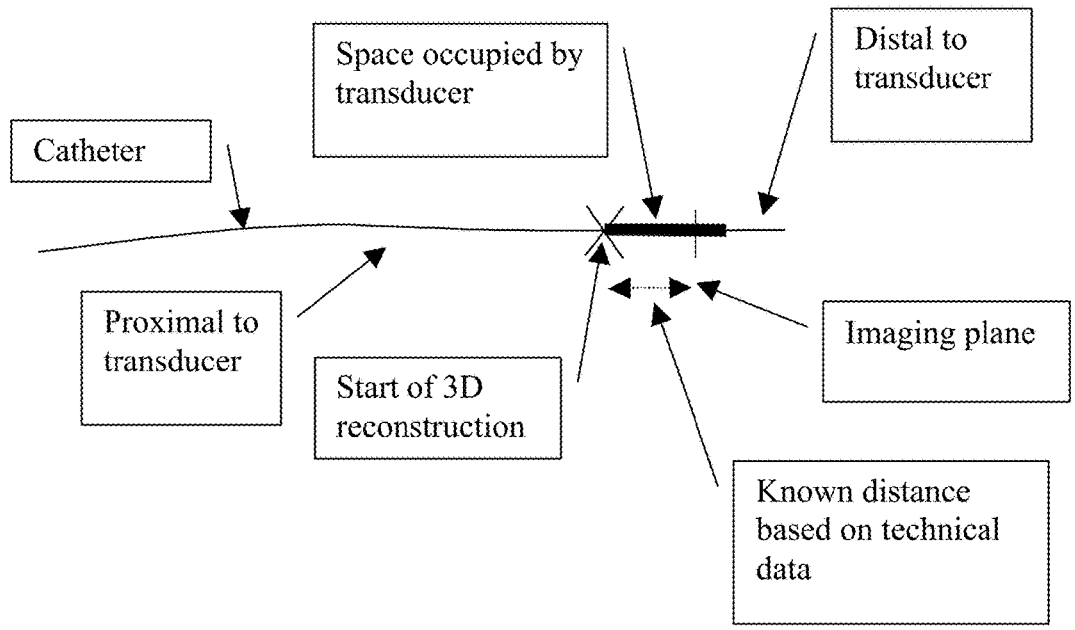
FIG. 7 shows the available information on the distance to the imaging plane with respect to a position on proximal side or distal side of an intravascular transducer.
Figure 8:
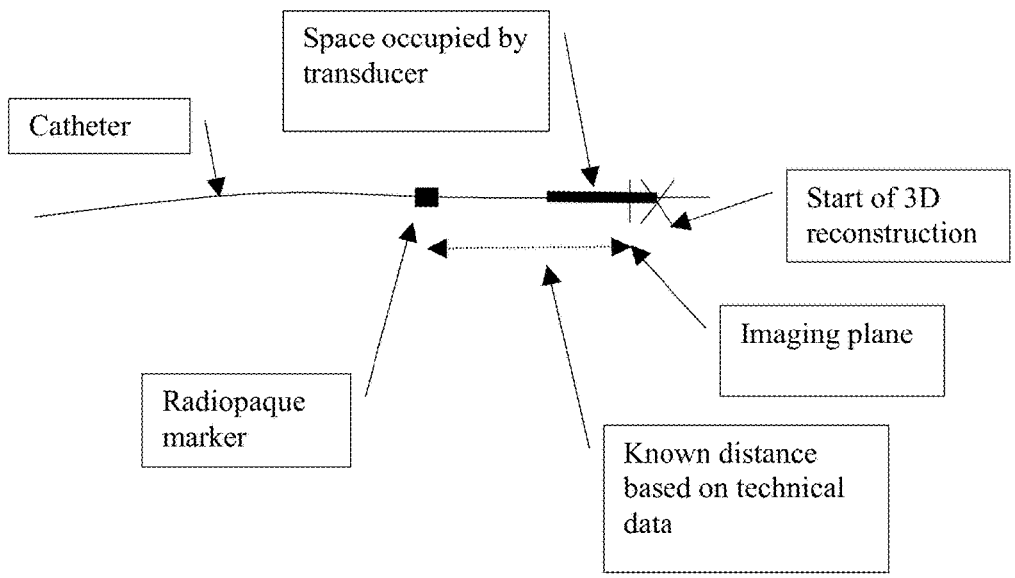
FIG. 8 shows the available information on the distance to the imaging plane with respect to a marker proximal or distal to the imaging plane.

Two situations can be distinguished:

1. Information is available on the distance to the imaging plane with respect to a position on proximal side or distal side of the transducer as exemplified in FIG. 7; and 2. Information is available on the distance to the imaging plane with respect to a radiopaque marker proximal or distal to the imaging plane as exemplified in FIG. 8.

In the first situation, the start of the 3D model is repositioned taking into account the distance of the imaging plane.

In the second situation, the user identifies the radiopaque marker, for example by the second node which is used for fitting the Catmull-row spline, or by indicating this radiopaque marker by right mouse click instead of left mouse click in which the remaining nodes are positioned. An automatic marker detection algorithm can be equally employed as, for instance, as disclosed in U.S. Pat. No. 8,411,927. With this information, the start of the 3D model can be repositioned by using the known distance from the technical description of the intravascular device. An example of an IVUS device which is accompanied by such description is the one manufactured by Volcano Corporation with the commercial name Eagle Eye® Platinum RX Digital IVUS Catheter.

Step 5: Perform Co-Registration of X-Ray Imaging and Intravascular Imaging

Since the relation to the first intravascular image has been established by the first position within the 3D reconstruction of the intravascular catheter path, by indication of the transducer as the first point of both 2D paths or by incorporating the technical data of the intravascular device, co-registration between X-ray and intravascular is automatically performed.

The co-registration can be performed after the intravascular pullback or just before the intravascular pullback. The latter allows real-time feedback of position of intravascular image in the X-ray images during the intravascular pullback.

Step 6: Perform Intravascular Pullback

In intravascular imaging the pullback method consists of initially positioning the intravascular transducer, or catheter tip, distal in a vessel of interest and pull the catheter tip with a controlled speed to the proximal part of the vessel of interest. During this pullback the intravascular transducer acquires intravascular images.

To match the spatial position of each intravascular image with respect to the X-ray image information on the pull back speed during its path from distal to proximal is required. In case of a motorized intravascular pullback, the registration is performed by computing the frame speed and matching each intravascular frame to the length of the 3D intravascular catheter path.

This means that for each intravascular image, its length with respect to the first intravascular frame is known and will be matched to the length obtained from the 3D intravascular catheter path. Its position with respect to the X-ray image is indicated by back projection of the corresponding 3D position within the 3D intravascular catheter path.

In case of a manual intravascular pullback, the motion of the intravascular device can be recorded to obtain information of the pullback speed during its path from distal to proximal. This can be accomplished, for example, by measuring the longitudinal motion of the intravascular catheter by means of a motion measurement system. Registration between X-ray and intravascular imaging can be performed by matching each intravascular frame, by using the recorded longitudinal motion i.e. the inter-frame distance, to the length of the 3D intravascular catheter path starting from the distal position of the 3D intravascular path.

Figure 9:
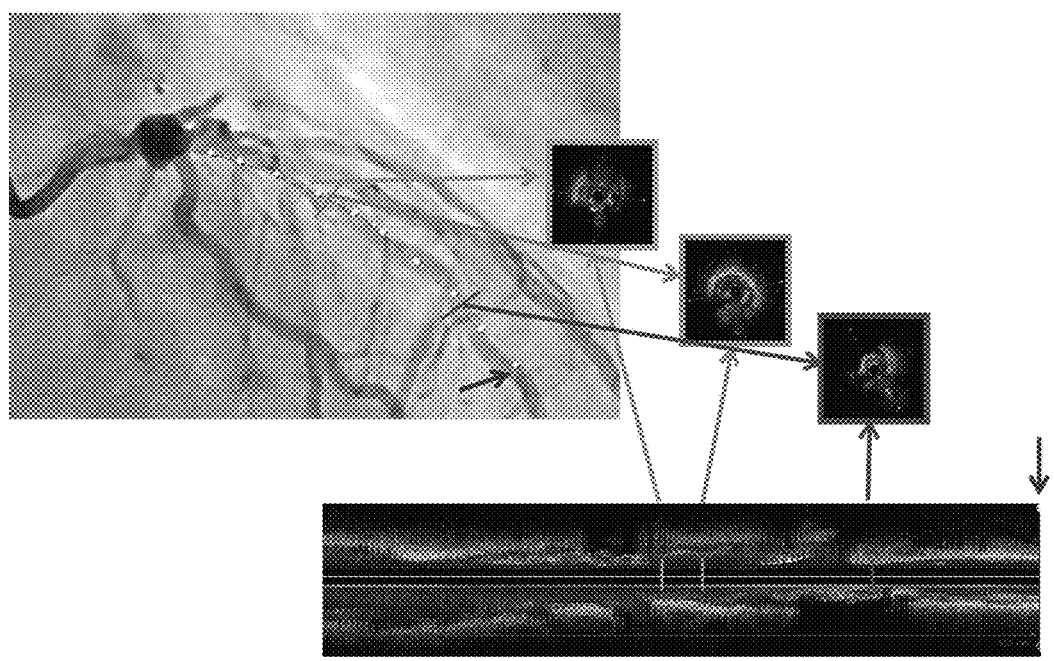
FIG. 9 shows the co-registration between IVUS and angiography. The bottom part of the figure shows a so called longitudinal image, i.e. a view in which all the IVUS frames are stack on each other and a cross section is made longitudinal. Corresponding position of IVUS frame in longitudinal view and angiographic view are visualized by markers. Arrow identifies the start of first IVUS frame and its position in the angiographic image.

FIG. 9 shows an example of co-registration between IVUS and angiography. Bottom figure illustrates a so-called longitudinal image. This is a view in which all the IVUS frames are stacked on each other and a cross section is made longitudinal. Corresponding position of IVUS frame in longitudinal view and angiographic view are visualized by markers. Arrow identifies the start of first IVUS frame and its position in the angiographic image. The same can also be performed on the fluoroscopic image.

In case the intravascular imaging is performed after the 3D reconstruction of the catheter path, the location of the intravascular transducer can be indicated real time on the X-ray image.

After co-registration is performed the physician can accurately define length measurements in both the X-ray angiographic image as well as in a longitudinal view of the intravascular image data. Furthermore, detailed vessel information from the intravascular image is accurately correlated its location in the X-ray angiographic image.

According to an improvement, the invention also provides information on the perpendicularity of the acquired intravascular images with respect to the vessel. Since the 3D trajectory of the intravascular transducer is known, a plane perpendicular at a position within this 3D trajectory can be back-projected on the X-ray angiographic image allowing the physician to view the perpendicularity of the intravascular image with respect to the vessel. The severity of mismatch in the 2D X-ray imaging viewing direction of perpendicularity can be visualized and/or quantified, for instance, by means of colour coding the back-projected line. In case the intravascular image is not perpendicular to the vessel, the cross sectional area of the vessel in IVUS and/or OCT images will be overestimated.

Figure 10:
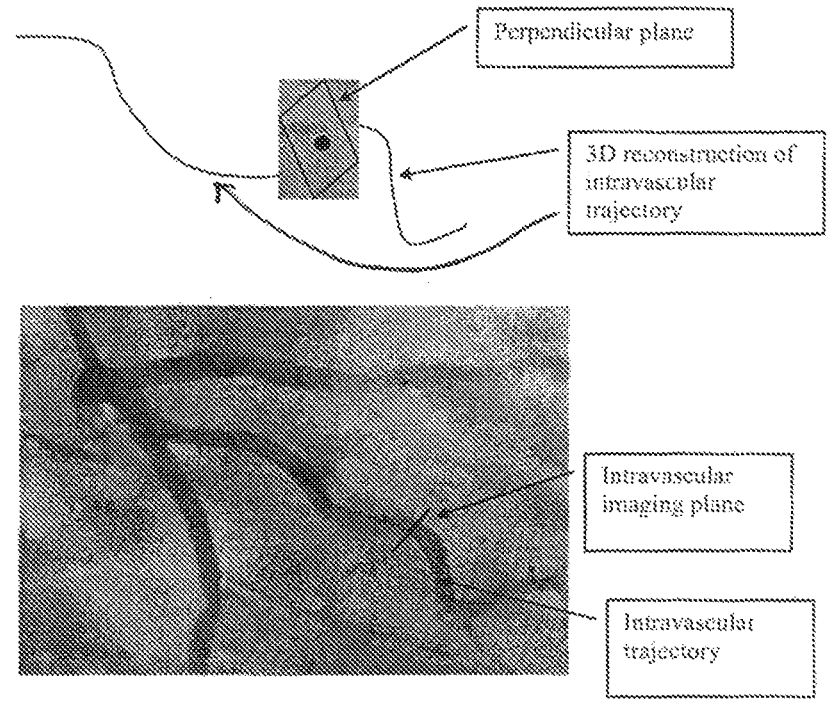
FIG. 10 shows an example of a visualization of a perpendicular intravascular imaging plane.

FIG. 10 shows an example of a visualization of a perpendicular intravascular imaging plane.

Figure 11:
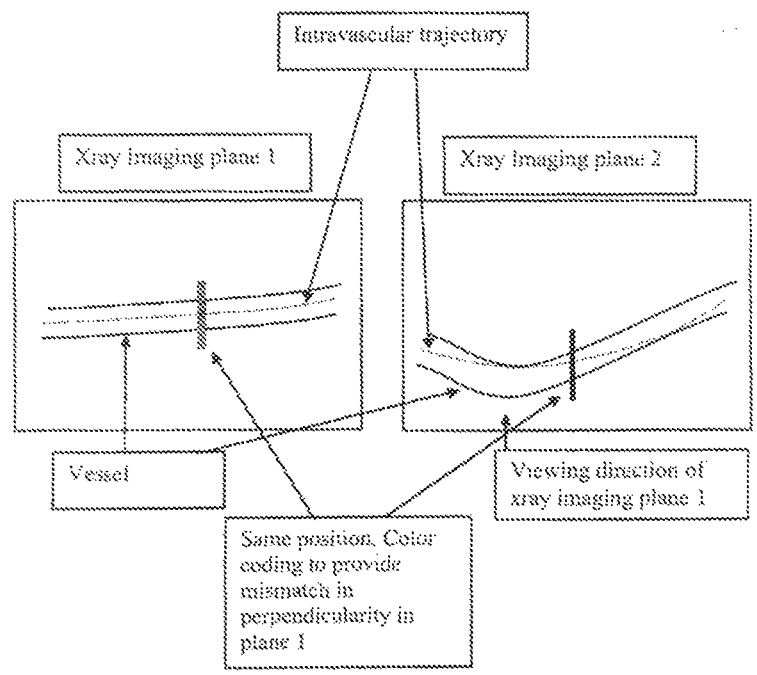
FIG. 11 shows an example of a visualization of a non-perpendicular intravascular imaging plane in case of mismatch in the 2D X-ray imaging viewing directions.

FIG. 11 shows an example of a visualization of a non-perpendicular intravascular imaging plane in case of mismatch in the 2D X-ray imaging viewing directions.

The invention has been mainly disclosed with reference to co-registration of intravascular images and X-ray angiographic images. A person of ordinary skill in the art will appreciate that this teaching can be equally extended to cover co-registration of images made with any imaging or measuring device that travels through any tubular object with images taken from outside the object with any type of imaging modality including X-ray, MRI, SPECT, Ultrasound or the like. For example in case of registration of IVUS images with ultrasound images taken from outside the object as in normally echography practice, the same apparatus can be used to reconstruct both types of images thus providing a very compact system.

The same system could also provide the actuating commands to perform pullback at a known speed starting at a known instant of time thus increasing manoeuvrability and repeatability.

Further to vessels, examples of tubular objects may be the oesophagus, the intestine or the bronchitis in the medical field, and any kind of pipe in general in the field of non-destructive testing.

Figure 12:
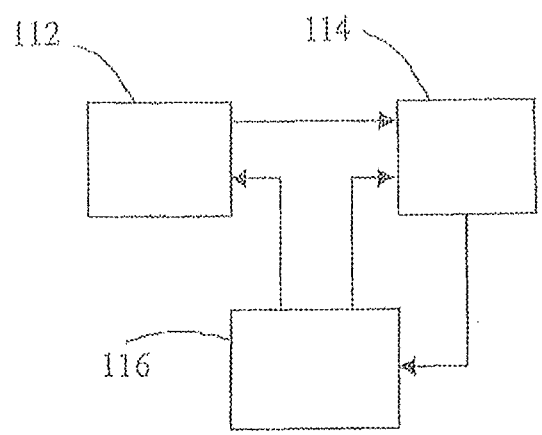
FIG. 12 is a functional block diagram of an exemplary system for registering angiography and intravascular images of a vessel.

FIG. 12 is a functional block diagram of an exemplary system for registering angiography and intravascular images of a vessel, which includes an imaging apparatus 112 that operates under commands from user interface module 116 and will provide data to data processing module 114. The imaging apparatus 112 acquires intravascular images of the vessel organ of interest. The imaging apparatus 112 includes an intravascular device that is deployed in the vessel to a start of examination location for acquiring images of the vessel when pulling back the device from such location. The pulling back is performed at a controlled speed through a motorized pulling element. The data processing module 114 may be realized by a personal computer, workstation or other computer processing system. The data processing module 114 processes the images acquired by the imaging apparatus 112 to generate data as described herein. The user interface module 116 interacts with the user and communicates with the data processing module 114. The user interface module 116 can include different kinds of input and output devices, such as a display screen for visual output, a touch screen for touch input, a mouse pointer or other pointing device for input, a microphone for speech input, a speaker for audio output, a keyboard and/or keypad for input, etc. The data processing module 114 and the user interface module 116 cooperate to carry out the operations of FIGS. 2 and 3 as described herein.

Figure 13:
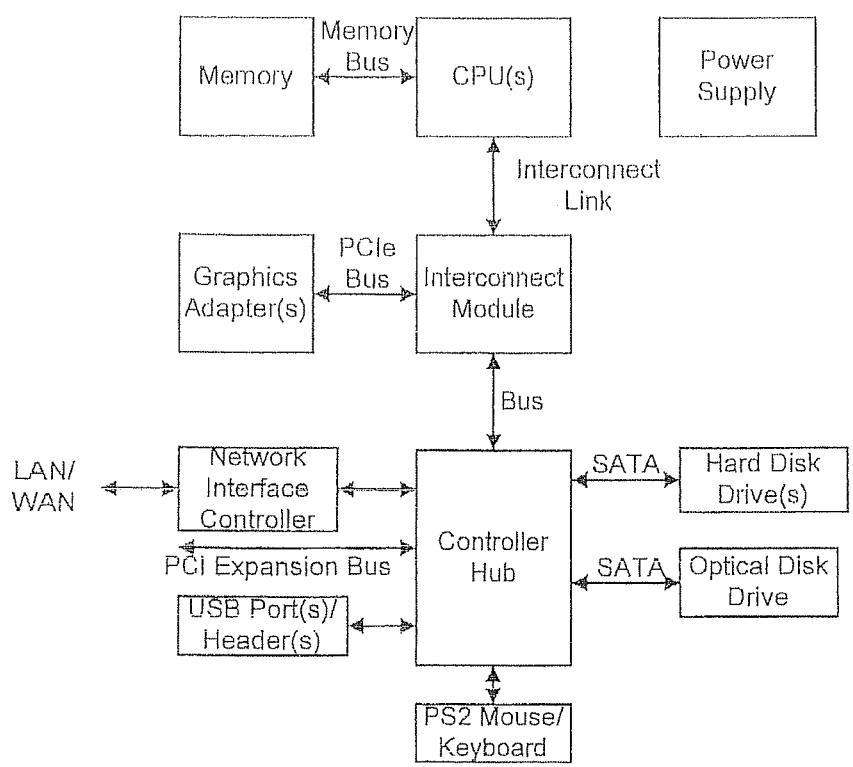
FIG. 13 is a schematic block diagram of a computer workstation.

The operations of FIGS. 2 and 3 can also be carried out by software code that is embodied in a non-transitory computer-readable storage medium (a computer product such as, an optical disc or other form of persistent memory such as a USB drive or a network server). The software code can be directly loadable into the memory of a data processing system, such as the computer workstation of FIG. 13, for carrying out the operations of FIGS. 2 and 3, as described herein.

There have been described and illustrated herein an embodiment of a method for tracking objects in a target area of a moving organ from sequences of consecutive image frames of such organ. While particular embodiments have been described, it is not intended that the claims be limited thereto, as it is intended that the claims be as broad in scope as the art will allow and that the specification be read likewise. It will therefore be appreciated by those skilled in the art that yet other modifications could be made to the disclosed embodiment without deviating from its spirit and scope as claimed.

What is claimed is:

1. A method for co-registration of two-dimensional (2D) angiography images and intravascular images of a vessel, of which the intravascular images are in the form of a sequence of images obtained from an intravascular imaging device which is pulled back through the vessel, the method comprising:
   a) generating a three-dimensional (3D) reconstruction of a path of the intravascular device within the vessel from a plurality of the 2D angiography images of the vessel which have been obtained from different perspectives, wherein the 3D reconstruction of the path of the intravascular device within the vessel is determined by 3D reconstruction of a catheter wire that extends from the intravascular device;
   b) determining a first position of an element of the intravascular device within the 3D reconstruction of the path of the intravascular device within the vessel;
   c) correlating the first position of the element of the intravascular device with a correspondent point in the 3D reconstruction of the path of the intravascular device within the vessel; and
   d) correlating each intravascular image of the sequence with a corresponding spatial position within at least one of the 2D angiography images.

2. The method according to claim 1, wherein a) comprises determining the path of the intravascular device within the vessel in at least two 2D angiography images of the vessel either automatically or manually by fitting user indicated points.

3. The method according to claim 1, wherein the 2D angiography images include 2D X-ray images obtained with or without contrast agents.

4. The method according to claim 3, wherein the 2D angiography images include a fluoroscopic image obtained without contrast agents.

5. The method according to claim 1, wherein the 2D angiography images include a first 2D angiography image and a second 2D angiography image, the second 2D angiography image being selected to match a cardiac phase of the first 2D angiography image by means of ECG matching.

6. The method according to claim 1, wherein the 3D reconstruction of the path of the intravascular device within the vessel starts from a point related to the first position of the element of the intravascular device in at least two 2D angiography images of the vessel.

7. The method according to claim 1, wherein d) involves correlating position of the element of the intravascular device based on intravascular frame speed or intravascular pullback speed and intravascular elapsed imaging time.

8. The method according to claim 1, wherein d) involves correlating position of the element of the intravascular device based on recorded motion during pull back.

9. The method according to claim 1, wherein the intravascular device has an imaging plane, the element of the intravascular device being a marker or any position on proximal side or distal side of the intravascular device having a known distance to such imaging plane.

10. The method according to claim 9, wherein the 3D reconstruction of the path of the intravascular device within the vessel has a starting point related to a position of the imaging plane of the intravascular device before pull back.

11. The method according to claim 10, wherein the imaging plane of the intravascular device is identified by receiving from a user a position of a radiopaque marker as a left mouse click on a node of a fitting Catmull-row spline, the marker being identified by a right mouse click.

12. The method according to claim 1, further comprising showing a longitudinal image which includes intravascular images acquired during pull back stacked on each other along a longitudinal line, the position of each intravascular image of the stack within the vessel being identified by a marker on the line and a corresponding marker in the 2D angiography image.

13. The method according to claim 1, wherein a degree of perpendicularity of the intravascular images with reference to the vessel is determined by calculating planes perpendicular to the 3D reconstruction of the path of the intravascular device within the vessel and back projecting such planes on the 2D angiography image.

14. The method according to claim 13, wherein the degree of perpendicularity is evaluated by comparing orientation of planes perpendicular to the 3D reconstruction of the path of the intravascular device within the vessel with orientation of corresponding planes perpendicular to a lumen boundary of the vessel on the 2D angiography image.

15. The method according to claim 14, wherein orientation of the planes perpendicular to the 3D reconstruction of the path of the intravascular device within the vessel and to the lumen boundary are shown as markers in the form of segments on the 2D angiography image.

16. The method according to claim 13, wherein the degree of perpendicularity is quantified using a colour coded representation on the 2D angiography image.

17. A non-transitory computer-readable storage medium storing an executable computer program for causing a computer to execute a method for co-registration of two-dimensional (2D) angiography images and intravascular images of a vessel, of which the intravascular images are in the form of a sequence of images obtained from an intravascular imaging device which is pulled back through the vessel, the method comprising:
   a) generating a three-dimensional (3D) reconstruction of a path of the intravascular device within the vessel from a plurality of the 2D angiography images of the vessel which have been obtained from different perspectives, wherein the 3D reconstruction of the path of the intravascular device within the vessel is determined by 3D reconstruction of a catheter wire that extends from the intravascular device;
   b) determining a first position of an element of the intravascular device within the 3D reconstruction of the path of the intravascular device within the vessel;
   c) correlating the first position of the element of the intravascular device with a correspondent point in the 3D reconstruction of the path of the intravascular device within the vessel; and
   d) correlating each intravascular image of the sequence with a corresponding spatial position within at least one of the 2D angiography images.

18. A system for registering two-dimensional (2D) angiography and intravascular images of a vessel, comprising:
   an imaging apparatus for acquiring intravascular images of the vessel;
   a computing device comprising a processor and a memory, wherein the memory stores instructions that, when executed by the processor, cause the computing device to store and/or receive at least two 2D angiography images of the vessel and to register the intravascular images with at least one of the 2D angiography images,
   wherein the imaging apparatus comprises an intravascular device to be deployed in the vessel to a start of examination location for acquiring a sequence of intravascular images of the vessel when pulling back the intravascular device from the start of examination location, said pulling back being performed at a controlled speed through a motorized pulling element, and
   wherein the instructions stored in the memory of the computing device, when executed by the processor, further cause the computing device to:
   a) generate a three-dimensional (3D) reconstruction of a path of the intravascular device within the vessel from a plurality of 2D angiography images of the vessel which have been obtained from different perspectives, wherein the 3D reconstruction of the path of the intravascular device within the vessel is determined by 3D reconstruction of a catheter wire that extends from the intravascular device;
   b) determine a first position of an element of the intravascular device within the 3D reconstruction of the path of the intravascular device within the vessel;
   c) correlate the first position of the element of the intravascular device with a correspondent point in the 3D reconstruction of the path of the intravascular device; and
   d) correlate each intravascular image of the sequence with a corresponding spatial position within at least one of the 2D angiography images.

19. The system according to claim 18, wherein the combination device has an input to receive from the intravascular device-frame speed or intravascular pullback speed and intravascular elapsed imaging time or recorded motion, the combination device being configured to read and process such input to correlate the position of the element of the intravascular device in the 3D reconstruction of the path of the intravascular device within the vessel during said pulling back.

20. The system according to claim 18, wherein the intravascular device has an imaging plane, the element of the intravascular device being a marker or any position on proximal side or distal side of the intravascular device having a known distance to such imaging plane.

21. The system according to claim 18, wherein the 3D reconstruction of the path of the intravascular device within the vessel has a starting point related to the start of examination position of the intravascular device in a 2D angiography image of the vessel.

22. The system according to claim 18, in combination with an X-ray apparatus for acquiring two or more 2D angiography images of a vessel of a patient from different perspectives.

23. The system according to claim 22, wherein the X-ray apparatus is a dual arm X-ray apparatus to acquire biplane angiography images or a single arm X-ray apparatus to acquire single plane fluoroscopic and/or angiographic images.

24. The system according to claim 22, wherein the combination device is configured to perform the method according to claim 1 to register intravascular images with at least one 2D angiographic image.

25. A system for registering two dimensional (2D) angiography images and a sequence of intravascular images of a vessel, the system comprising:
   a processor; and
   a memory including instructions that, when executed by the processor cause the system to:
   a) generate a three-dimensional (3D) reconstruction of a trajectory of an intravascular device within the vessel from a plurality of 2D angiography images of the vessel which have been obtained from different perspectives, wherein the 3D reconstruction of the path of the intravascular device within the vessel is determined by 3D reconstruction of a catheter wire that extends from the intravascular device;
   b) determine a first position of an element of the intravascular device within the 3D reconstruction of the path of the intravascular device within the vessel;
   c) correlate the first position of the element of the intravascular device with a correspondent point in the 3D reconstruction of the path of the intravascular device within the vessel; and
   d) correlate each intravascular image of the sequence of intravascular images with a corresponding spatial position within at least one of the 2D angiography images.

26. A method for co-registration of two-dimensional (2D) angiography images and intravascular images of a vessel, of which the intravascular images are in the form of a sequence of images obtained from an intravascular imaging device which is pulled back through the vessel, the method comprising:
   a) generating a three-dimensional (3D) reconstruction of a path of the intravascular device within the vessel from a plurality of the 2D angiography images of the vessel which have been obtained from different perspectives, wherein the 3D reconstruction of the path of the intravascular device within the vessel is determined by 3D reconstruction of a catheter wire that extends from the intravascular device; and b) matching a spatial position of an intravascular image of the vessel with respect to a 2D angiography image of the vessel based on a length of the 3D reconstruction of the path of the intravascular device within the vessel.

27. The method according to claim 26, wherein the 3D reconstruction of the path of the intravascular device within the vessel starts from a point related to position of an element of the intravascular device in a 2D angiography image of the vessel.

28. The method according to claim 1, wherein:
the 3D reconstruction of the intravascular catheter wire does not assume that the path of the intravascular catheter wire within the vessel follows the centerline of the vessel.

* * * * *